US008775210B2

(12) United States Patent
Bao et al.

(10) Patent No.: US 8,775,210 B2
(45) Date of Patent: Jul. 8, 2014

(54) ENTERPRISE IMAGING WORKLIST SERVER AND METHOD OF USE (75) Inventors: Yongjian Bao, Vernon Hills, IL (US); William Stoval, III, Mount Prospect, IL (US); Xiaofeng Xu, Des Plaines, IL (US)

(73) Assignee: General Electric Company, Schenectady, NY (US)

( * ) Notice: Subject to any disclaimer, the term of this patent is extended or adjusted under 35 U.S.C. 154(b) by 524 days.

(21) Appl. No.: 12/765,429

(22) Filed: Apr. 22, 2010

(65) Prior Publication Data
US 2010/0205011 A1 Aug. 12, 2010

Related U.S. Application Data (62) Division of application No. 11/158,835, filed on Jun. 22, 2005, now abandoned.

(51) Int. Cl.
*G06Q 50/00* (2012.01)
(52) U.S. Cl.
USPC .................................. 705/3; 705/2; 705/7.27
(58) Field of Classification Search
CPC ......................... G06F 19/321; G06F 17/3028
USPC .......................................... 705/2/3, 2–4, 7.27
See application file for complete search history.

(56) References Cited

U.S. PATENT DOCUMENTS

| | | | |
|---|---|---|---|
| 6,260,021 B1 * | 7/2001 | Wong et al. ........................ 705/2 |
| 6,287,257 B1 * | 9/2001 | Matichuk ....................... 600/437 |
| 6,574,742 B1 * | 6/2003 | Jamroga et al. ............... 713/400 |
| 7,028,182 B1 * | 4/2006 | Killcommons ................ 713/161 |
| 7,181,017 B1 * | 2/2007 | Nagel et al. .................... 380/282 |
| 7,411,693 B2 * | 8/2008 | Loukipoudis et al. ....... 358/1.15 |
| 7,555,720 B2 | 6/2009 | O'Rourke |
| 7,583,861 B2 * | 9/2009 | Hanna et al. ................... 382/305 |
| 7,756,724 B2 * | 7/2010 | Gropper et al. ..................... 705/2 |
| 7,831,683 B2 * | 11/2010 | Becker et al. .................. 709/217 |
| 2003/0005464 A1 * | 1/2003 | Gropper et al. ................. 725/115 |
| 2003/0115083 A1 | 6/2003 | Masarie, Jr. et al. |
| 2004/0015373 A1 | 1/2004 | Silva-Craig et al. |
| 2004/0086202 A1 * | 5/2004 | Short et al. ..................... 382/305 |
| 2005/0066002 A1 | 3/2005 | Teres et al. |
| 2005/0246629 A1 * | 11/2005 | Hu ................................... 715/513 |
| 2006/0122865 A1 | 6/2006 | Preiss et al. |
| 2006/0242159 A1 * | 10/2006 | Bishop et al. ................... 707/10 |

OTHER PUBLICATIONS

Non-final office action, issued by the United States Patent and Trademark Office in connection with U.S. Appl. No. 11/158,835, on Jul. 29, 2009, 14 pages.

* cited by examiner

*Primary Examiner* — Mark Holcomb
(74) *Attorney, Agent, or Firm* — Hanley, Flight & Zimmerman, LLC (57) ABSTRACT

Certain embodiments of the present invention provide a networked healthcare data management system. Certain embodiments of the data management system include a healthcare data archive connected to a network wherein the archived data comprises diagnostic, therapeutic, and demographic data. Certain embodiments further include a worklist server connected to the network wherein the worklist server receives data descriptors from the healthcare data archive and compiles the data descriptors into worklists. Certain embodiments also include a client system connected to a network wherein the client system queries the worklist server and the worklist server answers the queries by providing at least the network location of the archived data.

18 Claims, 5 Drawing Sheets

ENTERPRISE IMAGING WORKLIST SERVER AND METHOD OF USE

RELATED APPLICATIONS

This application is a divisional application of Ser. No. 11/158,853, filed Jun. 22, 2005, now pending. The disclosure of this prior application is incorporated herein by reference in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present system and method relate generally to electronic communications in a healthcare setting. Particularly, certain embodiments relate to providing scalable, procedure-centric management of patient data across multiple networked sites.

Healthcare facilities often employ certain types of digital diagnostic imaging modalities, such as computed tomography, magnetic resonance imaging, ultrasound imaging, and X-ray imaging. These digital diagnostic imaging modalities use a common format for image data, known as Digital Imaging and Communications in Medicine (DICOM). The evolution of the DICOM format facilitated the development and expansion of Picture Archiving and Communication Systems (PACS). Use of the DICOM semantics provided by the DICOM format has become the standard method for managing imaging data access in healthcare institutions.

The DICOM standard enumerates a command set, data formats, interface specifications, communication protocols, and command syntax. DICOM sets forth Information Objects (types of data, such as computerized tomography, magnetic resonance, x-ray, ultrasound, etc.), Service Classes (actions with data, such as send, receive, print, etc.), and data transmission protocols. DICOM application services provide the ability to transfer images and image related data between DICOM applications. A DICOM service-object pair (SOP) is used to push and/or pull information between DICOM applications.

As standalone systems in healthcare settings, PACS have a number of roles in data management. PACS receive image data sets fed from imaging modality devices. PACS manage storage systems for data persistency, managing both short-term and long-term storage. PACS accept query requests from client applications, enabling those client applications to retrieve specified data. PACS may also interface with other healthcare information systems.

Figure 1:
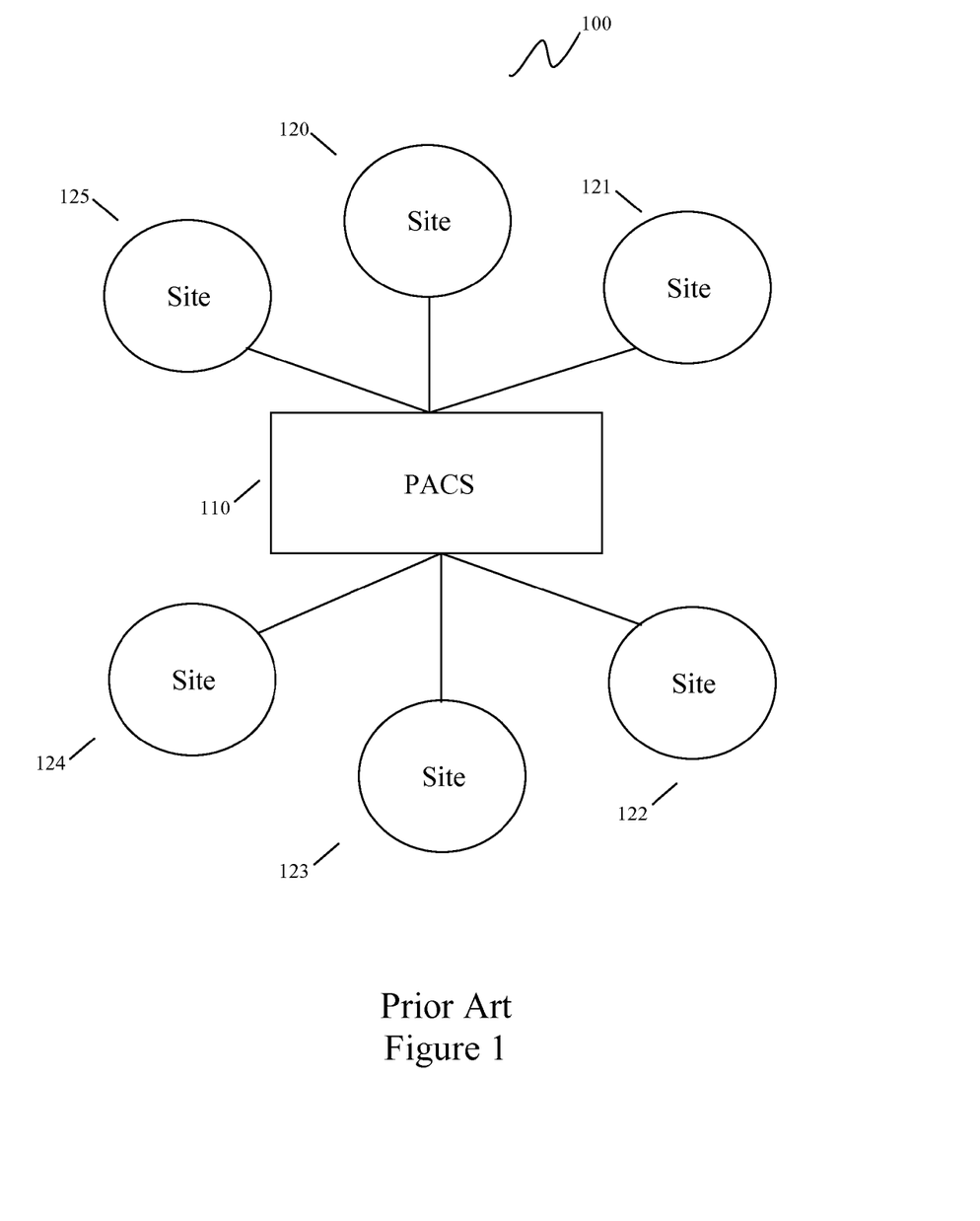
FIG. 1 illustrates a prior art system of data management across an enterprise having multiple sites using a centralized PACS.

Using PACS as centralized servers for DICOM format queries has greatly improved diagnostic image access and distribution in a heterogeneous systems environment. In the recent past, the PACS have been able to scale with the growth of healthcare networks and maintain an acceptable level of service. FIG. 1 illustrates a prior art system 100 for scaling access to a centralized PACS 110 across an enterprise that contains multiple sites 120, 121, 122, 123, 124 & 125. In FIG. 1, each site 120-125 connects directly with the PACS 110.

However, it is increasingly challenging to provide an image access solution across an entire healthcare network as these healthcare enterprises grow larger and more far-flung. There is a trend towards improved healthcare information accessibility in an expanding geographic scope: from departmental, to enterprise and inter-enterprise, and to regional and Independent Delivery Network environments.

However, scaling a central PACS to multiple sites can become extremely difficult as the number of sites significantly increases. A number of factors may prevent a single system from being scaled across multiple sites and enterprises, such as: data ownership; workflow complexity; system availability; and technology challenges.

One factor preventing enterprise scaling of a central PACS is data ownership. One reason that data ownership is a factor preventing enterprise scaling of a central PACS is that different institutions may not want to place data into a central repository. Also, different institutions may not be able to place data into a central repository for technical or regulatory reasons. Generally speaking, healthcare institutions are amenable to sharing data with other healthcare institutions, but these same healthcare institutions prefer to control access to data. The boundaries between and among healthcare institutions may create barriers for the creation of a central data repository.

Another factor preventing enterprise scaling of a central PACS is workflow complexity. Generally, workflow is another name for the pool of actions to be taken that originate when a radiologist or other healthcare professional places an order for work to be performed by an imaging modality on a particular patient and eventually saved on a PACS. Healthcare institutions create data management processes for handling workflow known as workflow models. Different healthcare institutions may adopt different workflow models. One potential consequence of these different workflow models is that a single procedure, which is common to many institutions, may be treated differently by different workflow models. These different workflow models for a single, common procedure create a challenge to provide efficient workflow management functions and tools to cope with various needs across multiple enterprises.

Still another factor preventing enterprise scaling of a central PACS is system availability. A single PACS or even a network of PACS may only be available to a limited number of users at a time. Thus, whether a user is archiving, retrieving, or otherwise managing data, the system resources of the PACS must be allocated among all the users demanding PACS access. When more healthcare institutions or other participating user sites are given access to one PACS or a PACS network, the system availability and reliability decreases. Scaling PACS access to an entire enterprise may decrease system availability dramatically.

Yet another factor preventing enterprise scaling of a central PACS can be generally referred to as technical complexity. When an image management system is scaled to provide service across an enterprise or multiple enterprises, response time, system serviceability, network configuration and many other factors become more complicated to manage.

While each of the above factors presents substantial challenges to scaling a central PACS, none of these factors absolutely limits the system scalability. That is, it is possible that some part of each of the factors may be addressed by, for example, scaling system resources in proportion to the scaling of the PACS service area. However, the cost of increasing system resources to provide for the scalability of a single PACS can quickly offset the benefit of improved image availability and accessibility in the large-scale environment. A more efficient approach for system scalability is needed.

Aside from the factors described above that present challenges to PACS scalability, there is another kind of challenge to providing PACS access across a single enterprise or multiple enterprises. This other challenge may be understood as the difference between how a typical clinical user sees data versus how a typical data management system sees data. The difference between these points of view is that a typical clinical user has a procedure-centric approach and a data management system has a device-centric or data-centric approach.

For example, a clinical user expects to view images in a clinical record oriented way. That is, a clinical user considers that the hierarchy of clinical data will roughly follow the model of the actual interaction a patient has with the healthcare institution, which generally is: patient, visit, order, service request, and procedures. This hierarchy is the backbone of the procedure-centric approach. The patient may make multiple visits. Each visit may result in one or more orders, which in turn may result in one or more service request per order. The service requests in turn generate one or more procedures. A procedure represents the most basic imaging service unit that is orderable, interpretable, and chargeable. Images are produced and reported in a procedure for certain diagnostic purpose, according to the procedure's specification.

An important aspect of the procedure-centric model is its universality. That is, clinical users at different healthcare institutions will apply the procedure-centric model as the hierarchy they use to consider clinical data, regardless of how the data is actually handled by their local data management system. Thus, the procedure-centric model represents a commonly known and applied hierarchy for clinical data. A procedure-centric approach for image access potentially allows clinical users at different healthcare institutions to view and interpret images in common with each other.

On the other hand, the DICOM information model organizes images and other SOP instances in the following hierarchy: patient, study, series, and SOP instance. Each of these hierarchical levels is specific to the DICOM standard, and together they form the backbone of the device-centric model. The hierarchical levels of DICOM are queried using a query/retrieve information model as part of the DICOM standard. While the DICOM model has made significant improvements to standardize the data storage structure and to ease data exchange, the DICOM model does not necessarily reflect a clinical record oriented, or procedure-centric, organization of clinical data. The procedure-centric model requires more data management logic, clinical intelligence and process flexibility than the DICOM model provides.

Although the hierarchical levels in the procedure-centric model may seem superficially similar to the hierarchical levels in the device-centric model, the two hierarchies are substantially different. For example, a DICOM study does not necessarily match to a procedure. For the purposes of data management, error reconciliation, and process complexity, several studies may be produced in a single procedure, and a number of procedures may share the same study. In addition, a study may include a number of series or a number of DICOM objects such as Gray Scale Presentation State (GSPS), Key Image Node (KIN), and Structured Report (SR) objects. These DICOM objects may also be known as data descriptors. In the DICOM model, the client system must interpret which objects, studies, or series are relevant and how they should be used. The DICOM model for data management directly exposes a "data store view" to the clinical user, which may not reflect the clinical record context of the images.

As presented in the previous description, there is a need for scalable healthcare data management systems. There is a need for these scalable healthcare data management systems to overcome the challenges associated with data ownership, workflow complexity, system availability, and technology management. There is a further need to present data to clinical users in a procedure-centric format.

BRIEF SUMMARY OF THE INVENTION

Certain embodiments of the present invention provide a networked healthcare data management system. Certain embodiments of the data management system include a healthcare data archive connected to a network wherein the archived data comprises diagnostic, therapeutic, and demographic data. Certain embodiments further include a worklist server connected to the network wherein the worklist server receives data descriptors from the healthcare data archive and compiles the data descriptors into worklists. Certain embodiments also include a client system connected to a network wherein the client system queries the worklist server and the worklist server answers the queries by providing at least the network location of the archived data.

Certain embodiments of the present invention involve a method for integrating patient data throughout at least one healthcare enterprise. Certain embodiments of the method for integrating patient data include submitting at least one descriptor identifying data to a worklist server which receives the descriptor, wherein the data comprises diagnostic, therapeutic, or demographic information and wherein the data resides in a database or a data archive. Certain embodiments of the method for integrating patient data also include creating at least one worklist residing on the worklist server using the at least one descriptor. Certain embodiments of the method for integrating patient data further include accepting a worklist query to the worklist server from a client system, wherein the worklist query comprises a request for data. Certain embodiments of the method for integrating patient data also include filling the worklist query using the at least one worklist, wherein the filled query includes information sufficient to identify the network location of the database or the data archive on which the requested data resides and returning the filled query from the worklist server to the client system.

Certain embodiments of the present invention relates to a method for translating healthcare data from a device-centric model of data management to a procedure-centric model of data management. Certain embodiments of the method for translating healthcare data from a device-centric model of data management to a procedure-centric model of data management include providing healthcare data to an archive on a network, wherein the healthcare data comprises image data and procedure data related to the image data and mapping the procedure data from the archive to a worklist server, wherein the mapping includes information about the relationship between the image data and the procedure data. Certain embodiments of the method for translating healthcare data from a device-centric model of data management to a procedure-centric model of data management also include organizing the procedure data into image worklists and enabling a client system to query the image worklists for the procedure data, wherein the query answer includes information sufficient to identify the network location of the image data related to the procedure data.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

Figure 2:
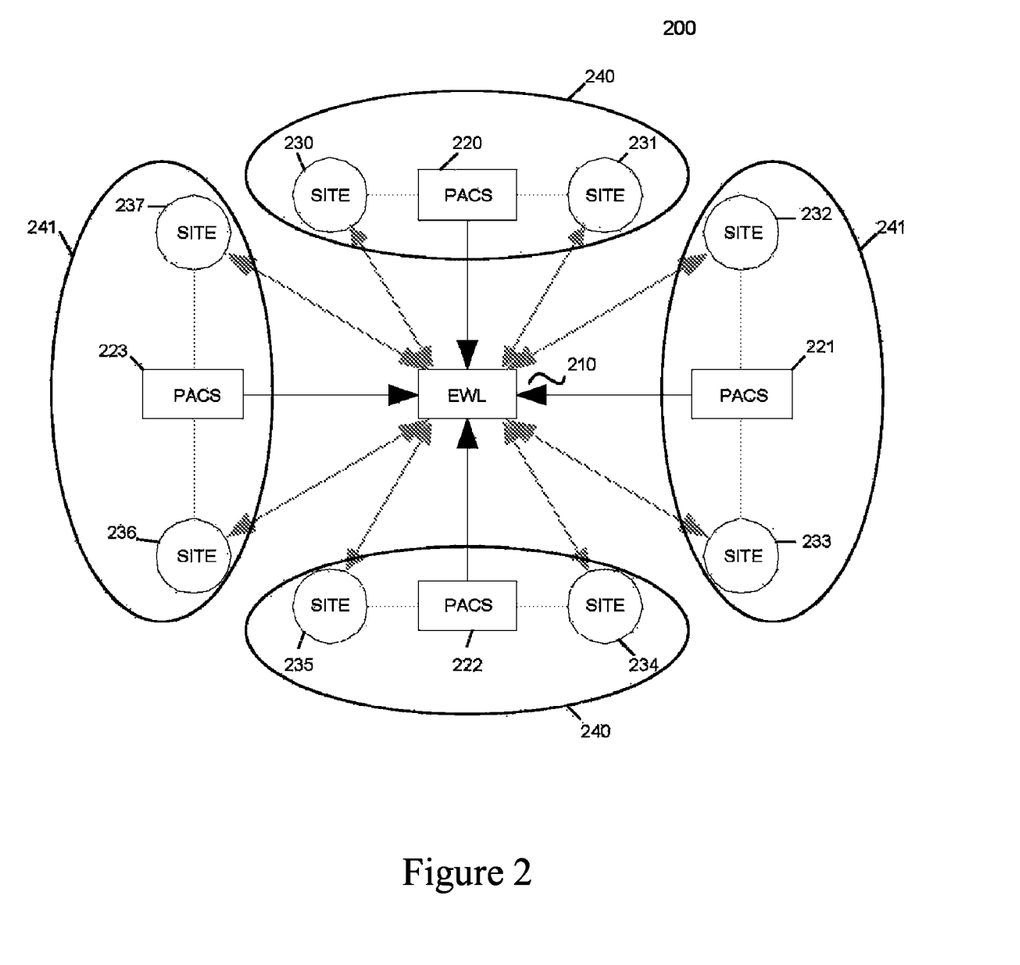
FIG. 2 illustrates a system using an enterprise worklist server to integrate multiple PACS and client sites across an enterprise according to an embodiment of the present invention.

FIG. 2 illustrates an embodiment of the present invention. In FIG. 2, a system 200 includes an Enterprise WorkList (EWL) server 210, which is connected with multiple PACS 220-223 and multiple sites 230-237. A site may include a diagnostic lab, an imaging suite, a clinic, a hospital, or other healthcare setting. In contrast with the prior art system 100 illustrated in FIG. 1 where all sites 120-125 are directly connected to a single PACS 110, in the embodiment illustrated in FIG. 2 certain PACS are directly connected only to certain sites. For example, PACS 220 is connected directly to site 230 and site 231, while PACS 221 is connected directly to site 232 and site 233. PACS 222 is connected directly to site 234 and site 235, and PACS 223 is connected directly to site 236 and site 237. These direct connections all contain two sites and one PACS, but embodiments of the present invention include those with more or fewer sites connected to one or more PACS.

The direct connections between certain sites and certain PACS illustrated in FIG. 2 allow for the workflows of each site remain locally managed. By managing the workflow locally, the overall architectural complexity of system 200 is reduced. Each set of sites and PACS can be seen as a organization domain 240-243 that interacts with EWL server 210.

The relationship between the organization domains 240-243 and EWL server 210 can be understood as a submit-publish structure. The submit-publish methodology will be described in more detail below. The system architecture of the submit-publish structure may provide a solution to many of the challenges preventing enterprise scaling of a PACS or a PACS network.

For example, the challenge of data ownership may be addressed by the relationship between organization domains 240-243 and EWL server 210 of the embodiment of the present invention illustrated in FIG. 2. Each PACS stores the data of the site or sites that are directly connected with that PACS. Thus, clinical data may still be locally owned by each healthcare institution participating in the enterprise. Further, the connection between EWL server 210 and each PACS 240-243 may be one-way such that each PACS 240-243 provides information to the EWL 210, but the EWL 210 does not provide user access back to a PACS 240-243. In this way, each healthcare institution participating in the enterprise may also maintain control over its clinical data.

Further, the challenge of workflow complexity may be addressed by the relationship between organization domains 240-243 and EWL server 210 of the embodiment of the present invention illustrated in FIG. 2. As mentioned above, organization domains 240-243 allow for workflow to be managed locally by each healthcare institution participating in the enterprise. This local management reduces the potential for conflicts arising from the different workflow models adopted by local healthcare institutions because the outputs from organization domains 240-243 to EWL server 210 do not necessarily depend on the workflow model adopted by the local healthcare institution.

Additionally, the challenge of system availability may be addressed by the relationship between organization domains 240-243 and EWL server 210 of the embodiment of the present invention illustrated in FIG. 2. For example, each organization domain 240-243 handles local workflow management, which frees resources of EWL server 210 to concentrate on handling worklist queries.

Moreover, the challenges of technical complexity may be addressed by the relationship between organization domains 240-243 and EWL server 210 of the embodiment of the present invention illustrated in FIG. 2. Since the actual clinical data continues to reside on individual PACS 220-223, the traffic between the organization domains 240-243 and EWL server 210 consists of smaller packets containing queries and answers rather than larger files containing actual data. Therefore, a greater number of sites may access an EWL server at the same time over a given network than if the sites were retrieving the actual clinical data from the EWL server. Also, the actual clinical data may be physically stored in separate locations from the organizational domains, such as in data archives. By decoupling the query systems from the physical storage systems, the architecture of EWL servers can be simplified and fewer network resources are required. Indeed, the architecture of organization domains and EWL servers allows for a number of EWL servers to become feeder systems to other EWL servers to build another layer into the hierarchy of enterprise data management.

Figure 3:
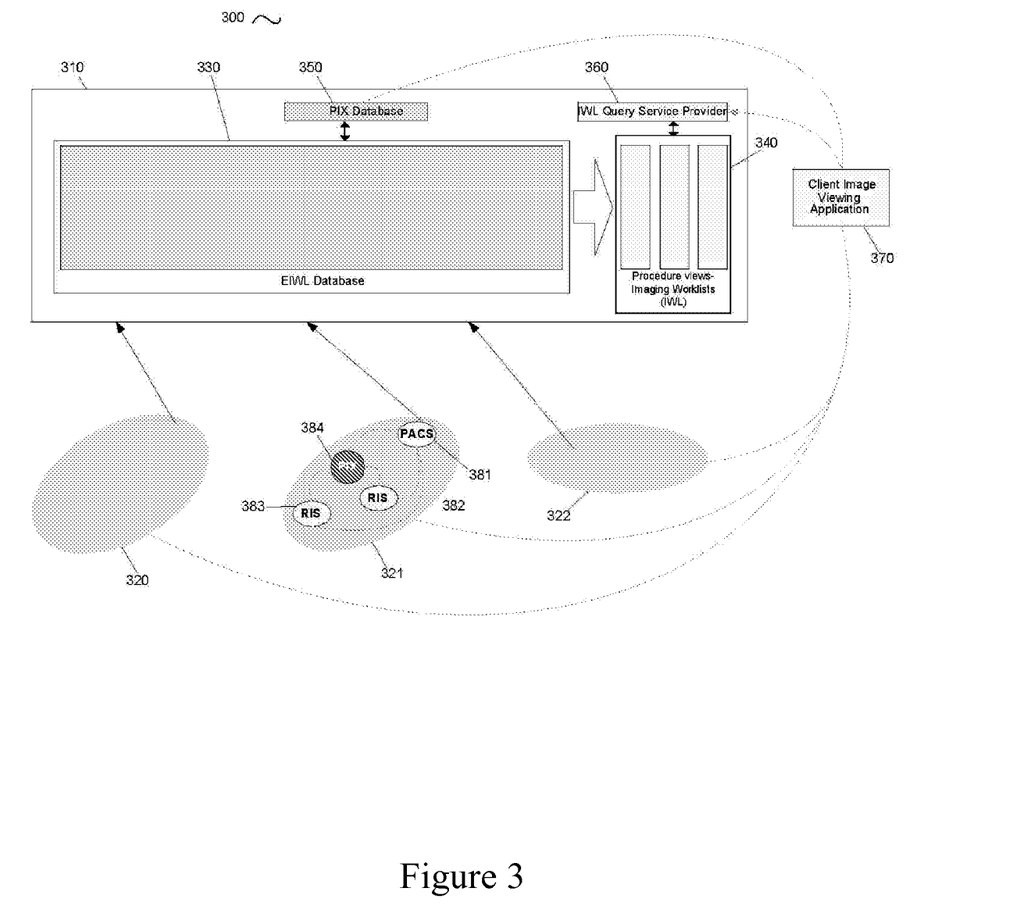
FIG. 3 illustrates a schematic for a system which provides scalable, procedure-centric clinical data according to an embodiment of the present invention.

FIG. 3 illustrates a schematic for a system which provides scalable, procedure-centric clinical data according to an embodiment of the present invention. System 300 includes organizational domains 320, 321 & 322, which are analogous to organizational domains 240-243 of FIG. 2. Organizational domains 320-322 are connected via a network to EWL server 310, which is analogous to EWL server 210 of FIG. 2. In the embodiment illustrated in FIG. 3, EWL server 310 includes EWL database 330, worklist engine 340, patient information database 350, and worklist query service provider 360. In other embodiments, EWL server 310 may include more or fewer databases, or databases containing different types of information. System 300 also includes image viewing application 370, which is connected via a network to organizational domains 320-322 and EWL server 310.

FIG. 3 further illustrates detail about the organizational domains, according to an embodiment of the present invention. Organizational domain 321 includes PACS 381, which is illustrated in this embodiment as being connected locally to scheduling systems 382 & 383. Scheduling systems 382 & 383 may be accessed by clinical users to schedule procedures for a patient. One example of a scheduling system typically found in a healthcare institution is a Radiology Information System (RIS). PACS 381 and scheduling systems 382 & 383 may also be connected via a local network to patient information crosslink (PIX) 384. For simplicity, FIG. 3 illustrates only the detail inside organizational domain 321, but it is understood that any organizational domains may have a similar structure to the one illustrated for organizational domain 321.

The system illustrated in FIG. 3 may provide certain advantages. For example, patient records common to a given patient may be identified in different patient information databases within different organization domains. The patient information crosslink helps manage this patient information within an organizational domain, and the EWL server may help reconcile this patient information across organizational domains. In addition, the EWL server may be able to resolve procedure message conflicts across different organizational domains, and may provides a consistent list of procedures to clinical users and client systems.

Figure 4:
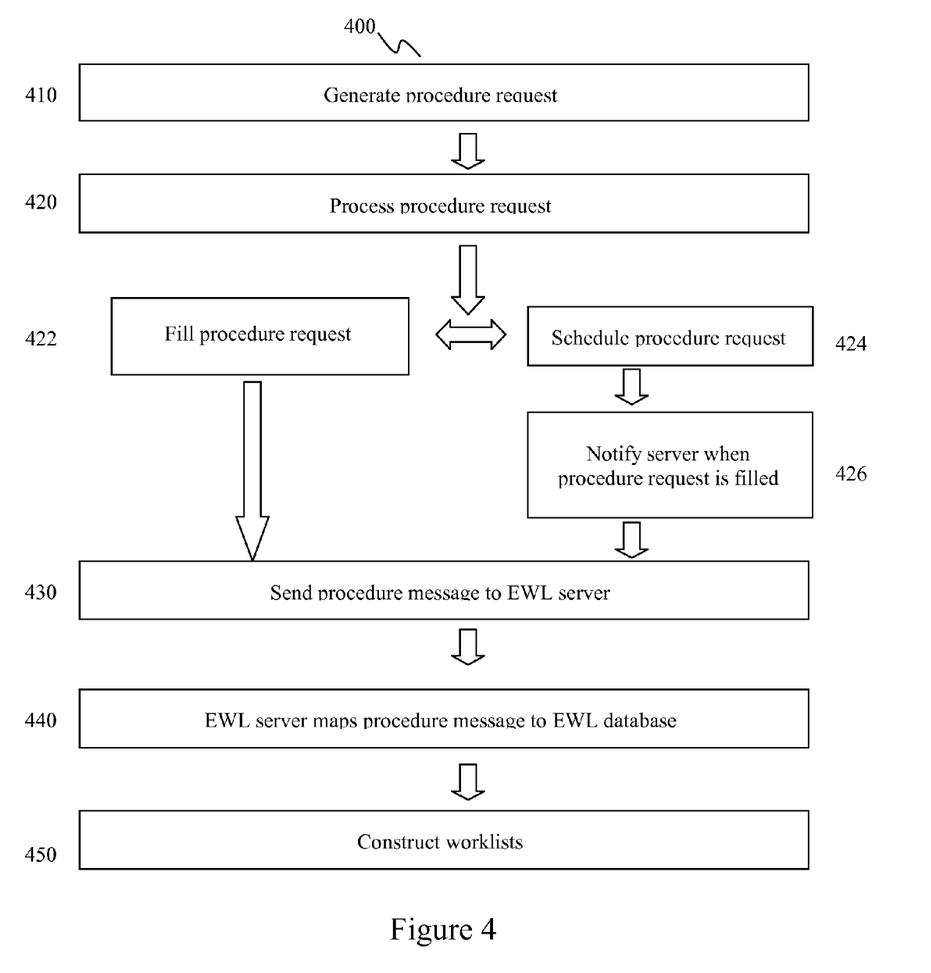
FIG. 4 illustrates a flow diagram for a method for translating clinical data from a device-centric model to a procedure-centric model according to an embodiment of the present invention.

FIG. 4 illustrates a flow diagram 400 for a method for translating clinical data from a device-centric model to a procedure-centric model according to an embodiment of the present invention. A procedure request is generated by a clinical user inside an organizational domain in step 410. A procedure request is processed inside an organizational domain in step 420. Processing of a request may include actually filling a procedure with a scheduled order carried out, for example, by imaging a patient using an imaging modality and storing an image as in step 422. An image may be stored on a PACS, or it may be stored in an image archive outside of the organizational domain, but still connected via a network to an organizational domain. Alternatively, processing of a request may simply include scheduling a procedure for a later date as in step 424. In a case where a request is simply scheduled for the future, a PACS may send an Instance Availability Notification (IAN) to an EWL server according to step 426. Additionally, an IAN helps manage the data availability in an EWL server when the image availability status changes in the future, for example, if archived media is removed from storage or a media defect is corrected.

Whether a request is processed by imaging a patient or simply by scheduling an imaging procedure in the future, a procedure message is sent to an EWL server according to step 430. Thus, although the time between a service request and performance of that request may be short or long, all service requests follow a "schedule-perform" paradigm. A procedure message may contain data descriptors which convey information including patient demographics, service request details, procedure information, and SOP instance references. SOP instance references may take the form of a Uniform Resource Locator (URL) or another reference format for locating an SOP instance on a network. A procedure message may also represent a specific view of a procedure dedicated to certain image distribution and viewing purposes defined by a PACS. An EWL server and all PACS share a set of coded concepts for message exchanges. Using these coded concepts for message exchanges, in addition to procedure records, a PACS may also submit a number of Procedure Views (PV) associated with a procedure as part of a procedure message in step 430.

According to step 440, an EWL server maps the procedure message to an EWL database. An EWL database stores information contained in a procedure message using a procedure-centric hierarchy, such as patient, visit, order, service request, and procedure. An EWL server provides access to the information from procedure messages by constructing worklists according to step 450. In a case where a procedure request is simply scheduled for the future as in step 424, an EWL server may indicate availability status of the SOP instances referenced in worklists of step 450 by including IAN messages in the information contained in a worklist. Because an EWL server may construct many different types of worklists, an EWL server may provide access control, such that certain users may only query certain worklists. For example, an EWL server may generate a worklist created for a certain medical specialty, and only users in that specialty area would be able to query this specialty worklist. A query process for users is more fully described in FIG. 5.

Figure 5:
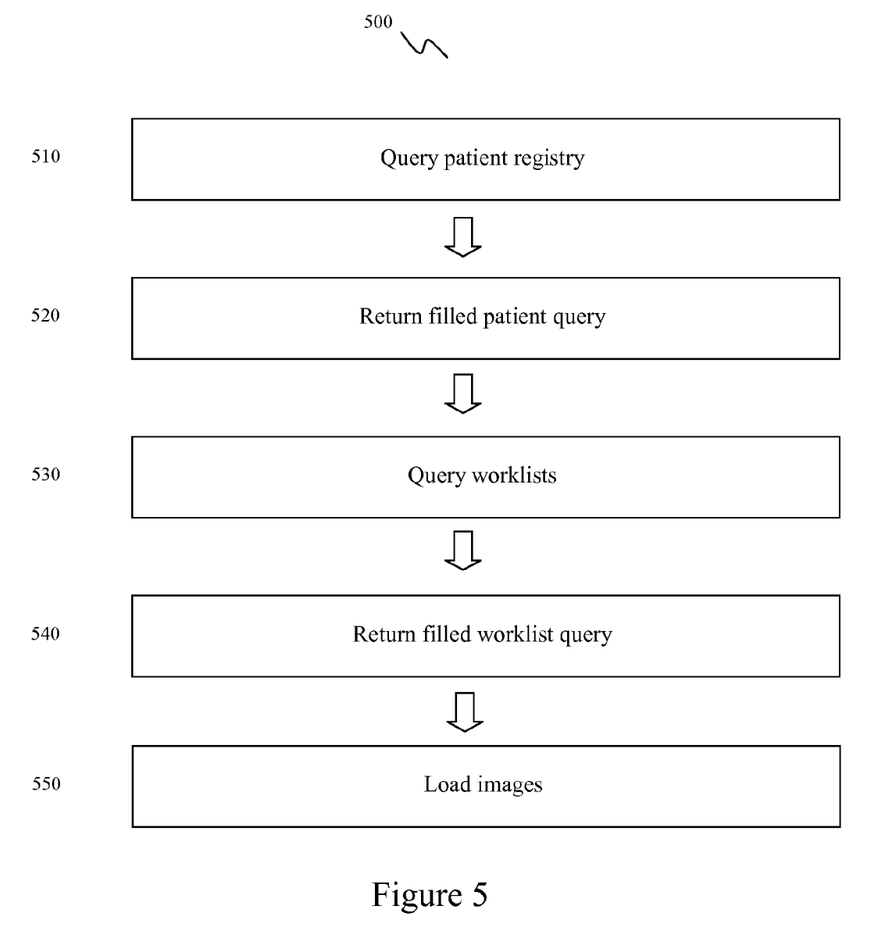
FIG. 5 illustrates a flow diagram for a method of retrieving data from an enterprise worklist server according to an embodiment of the present invention.

FIG. 5 illustrates a flow diagram 500 for a method of retrieving data from an enterprise worklist server according to an embodiment of the present invention. A client system queries a patient registry with some type of patient demographic information according to step 510. A patient information database, optionally in conjunction with a PIX, provides any supplemental information missing from the patient demographic information, according to step 520. The now-completed patient information may be returned to a client, or it may be combined with a worklist query that a client sends to an EWL server according to step 530. In step 530, a client sends a query to an EWL server. An EWL server fills a query using worklists generated, for example, according to FIG. 4, by using a query-filling algorithm.

A query-filling algorithm may be one of any number of known query-filling algorithms. In certain embodiments, a query-filling algorithm may employ a query-by-example model. In query-by-example, a complete data set is compared to an incomplete data set. An incomplete data set contains enough information that all parts of a complete data set that have data that matches the data from the incomplete set may be located. Once located, a complete data set information may be used to fill in an incomplete data set.

Once a query has been filled, an EWL server returns a filled query to a client, according to step 540. Among the information that may be included in a query is a reference regarding a network location of clinical data that a client is seeking. For example, an SOP instance reference may take the form of a Uniform Resource Locator (URL). Using a reference returned in step 540, a client may then load an SOP instance directly from an organizational domain where an SOP instance is stored, according to step 550.

There are certain advantages or benefits that may accrue using embodiments of the present invention. For example, a PACS is responsible for patient and procedure information accuracy in a procedure message that is submitted to an EWL server. Thus, a PACS "owns" a procedure and may report any change to a procedure by either canceling or updating a procedure in an EWL server. This simple approach of PACS "ownership" over procedures keeps patient and procedure information synchronized between EWL servers and PACS and/or organizational domains.

Further, an EWL server may provide an interface for a client from any organization domain to query worklists (with proper authentication and authorization). A worklist provides the most up-to-date patient and procedure information, and a worklist may overwrite the similar, but out-of-date, information in an SOP instance if there is a conflict between an SOP instance and a worklist.

By decoupling the clinical information management space and the SOP instance persistency space, the basic hierarchical unit of a procedure acts like a container, in which SOP instances may be placed based on their clinical record context. Errors occurring in the data acquisition phase, such as a wrong patient name, or wrong exam code, may be fixed by remapping the container-contents relationship. This procedure-centric approach enables image access with the latest patient and clinical context.

Therefore, using certain embodiments of the present invention, the images stored in the DICOM model may queried and data may be retrieved on the basis of procedure references. The clinical user may be able to view and interpret the retrieved data in a clinical diagnostic context.

EXAMPLE 1

An enterprise implements an image management system across multiple sites. Using an EWL server adds a very efficient alternative under certain circumstances. If a number of the sites manage their imaging interpretation workflow, data acquisition, and data storage locally, then a number of independent PACS may be deployed at each site. Each PACS may be connected with the EWL server to provide enterprise-wide imaging data access. Networking the PACS with the EWL server removes the performance and availability interdependency of sites that may occur if a single network solution was deployed, but still allows image access across multiple sites.

EXAMPLE 2

An enterprise seeks to share image data across more than twenty sites. Such a large enterprise would be unwieldy using current systems. However, an EWL server may connect to twenty or more PACS and provide a single view of the imaging data to the clinical user, as if the imaging data is managed in one system. In addition, the procedure-centric approach to image access may give the clinical user exactly the same experience of viewing images as when the images are viewed in a local PACS workstation.

EXAMPLE 3

An enterprise seeks to unify its image data management, but has various image handling platform from different vendors. This unification across different platforms is possible because the EWL server architecture is open. For each platform, different protocols may be implemented for procedure submission as well as for querying worklists based on unique procedure views. Thus, an enterprise image distribution environment may be created even though heterogonous image management system products operate at each site.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for translating healthcare data from a device-centric model of data management to a procedure-centric model of data management, comprising:
performing, by at least one computer processing device:
providing healthcare data received from an imaging modality to an imaging archive at one of a plurality of organizational domains, wherein each of the plurality of organizational domains comprises an associated imaging archive and at least one client system, wherein the healthcare data comprises image data and procedure data related to the image data, the healthcare data organized according to a device-centric model according to the imaging modality, the procedure data providing information regarding an imaging procedure with respect to the image data according to the device-centric model for the imaging modality, the device-centric model organizing the healthcare data in a device-centric hierarchy comprising patient, study, series, and service-object pair (SOP) instance for the imaging modality, wherein an SOP instance comprises information used to at least one of push and pull information between Digital Imaging and Communications in Medicine (DICOM) applications;
mapping the procedure data from the imaging archive to a worklist server, wherein the mapping includes information about the relationship between the image data and the procedure data, the worklist server mapping the procedure data using a procedure-centric hierarchy, wherein the worklist server is accessible to each of the plurality of organizational domains to map data from a plurality of device-centric models to the procedure-centric hierarchy, the mapping including taking the patient, study, series, and SOP instance information from the device-centric model and mapping to the procedure-centric hierarchy comprising patient, visit, order, service request, and procedure via the worklist server to decouple clinical information management from SOP instance persistency and place SOP instances within a procedure;
organizing the procedure data into image worklists based on the procedure-centric hierarchy; and
accepting submission of an image access query to the worklist server for the image data and the imaging procedure data related to the image data from at least one client system at one of the plurality of organizational domains, wherein the query answer from the worklist server includes the procedure data related to the image data and information to identify the network location of the image data at the imaging archive of the one of the plurality of organizational domains.

2. The method of claim 1 wherein the imaging archive is a Picture Archiving and Communications System (PACS).

3. The method of claim 1 further comprising mapping data to the worklist server relating to the availability status of the image data.

4. The method of claim 1 wherein the healthcare data further comprises patient demographic data.

5. The method of claim 1 wherein the procedure data further comprises Procedure Views (PV).

6. A method for managing the retrieval of medical imaging data across an enterprise connected via a network, comprising:
performing, by at least one computer processing device:
identifying diagnostic data related to a patient via an imaging modality at one of a plurality of organizational domains, wherein each of the plurality of organizational domains comprises an imaging archive and at least one client system, wherein the diagnostic data includes procedure messages and image data, and wherein the procedure messages provide information regarding an imaging procedure with respect to the image data according to a device-centric model for the imaging modality, the device-centric model organizing the diagnostic data according to a device-centric hierarchy comprising patient, study, series, and service-object pair (SOP) instance for the imaging modality, wherein an SOP instance comprises information used to at least one of push and pull information between Digital Imaging and Communications in Medicine (DICOM) applications;

transmitting via the network the procedure messages and the image data from the imaging modality to the imaging archive at the associated one of the plurality of organizational domains, wherein the imaging archive has a network location;

transmitting via the network the procedure messages from the imaging archive and the network location of the image data to a worklist server, wherein the procedure messages are organized in the device-centric hierarchy, wherein the worklist server is accessible to each of the plurality of organizational domains to map data from a plurality of device-centric models to the procedure-centric hierarchy;

mapping the procedure messages in the worklist server into a worklist having a procedure-centric hierarchy by reordering the device-centric procedure data into a procedure-centric format, wherein the mapping includes information about the relationship between the image data and the procedure data, the mapping including taking the patient, study, series, and SOP instance information from the device-centric model and mapping to the procedure-centric hierarchy comprising patient, visit, order, service request, and procedure via the worklist server to decouple clinical information management from SOP instance persistency and place SOP instances within a procedure;

accepting an image access query for image data at the worklist server from the at least one client system at one or more of the plurality of organizational domains connected to the network;

filling the query at the worklist server using the worklist; and returning an answer from the worklist server to the client system, wherein the answer includes data selected by the worklist server from the procedure-centric worklist and the network location at the imaging archive of the associated one of the plurality of organizational domains of the queried image data.

7. The method of claim 6, further comprising mapping the procedure messages into a plurality of work lists.

8. The method of claim 6, wherein the worklist server maps the procedure messages into a worklist specific to a medical specialty.

9. The method of claim 8, wherein the worklist specific to a medical specialty is used to fill a query from a specialist in the medical specialty.

10. The method of claim 9, wherein only specialists in the medical specialty are able to query the worklist specific to a medical specialty.

11. The method of claim 6; further comprising collecting diagnostic data from a single patient using a plurality of imaging modalities, wherein the diagnostic data includes procedure messages and image data.

12. The method of claim 11, wherein the procedure messages from the plurality of imaging modalities are mapped in the worklist server into a single worklist having a procedure-centric hierarchy by reordering the device-centric procedure data.

13. The method of claim 11, wherein the procedure messages from the plurality of imaging modalities are mapped in the worklist server into a plurality of worklists having a procedure-centric hierarchy by reordering the device-centric procedure data.

14. The method of claim 13, wherein each of the plurality of worklists is specific to a different medical specialty.

15. A non-transitory computer readable storage medium having encoded thereon a set of instructions which, when executed by a computer, perform the following:

an archiving routine that transmits procedure messages and image data collected using an imaging modality from the imaging modality to an imaging archive at one of a plurality of organizational domains, wherein each of the plurality of organizational domains comprises an associated imaging archive and at least one client system, and wherein the procedure messages provide information regarding an imaging procedure with respect to the image data according to a device-centric model for the imaging modality, the device-centric model organizing the procedure messages according to a device-centric hierarchy comprising patient; study; series; and service-object pair (SOP) instance for the imaging modality, wherein an SOP instance comprises information used to at least one of push and pull information between Digital Imaging and Communications in Medicine (DICOM) applications;

a submission routine that transmits procedure messages from the imaging archive at the associated one of the plurality of organizational domains to a worklist server on a network, the worklist server mapping the procedure data using a procedure-centric hierarchy, wherein the worklist server is accessible to each of the plurality of organizational domains to map data from a plurality of device-centric models to the procedure-centric hierarchy, wherein the mapping includes information about the relationship between the image data and the procedure data, the mapping including taking the patient, study, series, and SOP instance information from the device-centric model and mapping to the procedure-centric hierarchy comprising patient, visit, order, service request, and procedure via the worklist server to decouple clinical information management from SOP instance persistency and place SOP instances within a procedure;

a worklist-generating routine that reorders the procedure messages in the worklist server into at least one worklist based on the procedure-centric hierarchy, wherein the procedure messages are in a device-centric hierarchy and the worklist is in a procedure-centric hierarchy;

a query-filling routine that accepts at least one image access query for image data at the worklist server from a client system at one or more of the plurality of organizational domains and filling the query at the worklist server using the at least one worklist; and a query-answer routine that returns an answer from the worklist server to the client system, wherein the answer includes data selected by the worklist server from the worklist and a network location of the image data at the imaging archive of the one of the plurality of organizational domains.

16. The set of instructions of claim 15, wherein the worklist generating routine reorders the procedure messages in the worklist server into a plurality of worklists, wherein each of the plurality of work lists is specific to a different medical specialty.

17. The set of instructions of claim 15, wherein the query-filling routine identifies a medical specialty associated with the image access query.

18. The set of instructions of claim 15, further comprising a retrieval routine for transmitting image data from the imaging archive to the client system.

* * * * *